United States Patent
Ma et al.

(10) Patent No.: US 10,739,421 B1
(45) Date of Patent: Aug. 11, 2020

(54) SYSTEMS AND METHODS FOR TABLE MOVEMENT CONTROL

(71) Applicant: GE Precision Healthcare LLC, Wauwatosa, WI (US)

(72) Inventors: LiYa Ma, Beijing (CN); Kun Wang, Beijing (CN); Tao Wang, Beijing (CN)

(73) Assignee: GE PRECISION HEALTHCARE LLC, Wauwatosa, WI (US)

( * ) Notice: Subject to any disclaimer, the term of this patent is extended or adjusted under 35 U.S.C. 154(b) by 0 days.

(21) Appl. No.: 16/441,297

(22) Filed: Jun. 14, 2019

(51) Int. Cl.
*G01R 33/30* (2006.01)
*G01R 33/54* (2006.01)

(52) U.S. Cl.
CPC ......... *G01R 33/307* (2013.01); *G01R 33/543* (2013.01)

(58) Field of Classification Search
CPC .............................. G01R 33/307; G01R 33/543
See application file for complete search history.

(56) References Cited

U.S. PATENT DOCUMENTS

| | | | |
|---|---|---|---|
| 6,912,415 B2 | 6/2005 | Kruger et al. | |
| 6,975,113 B1 | 12/2005 | Gurr | |
| 7,346,383 B2 | 3/2008 | Riederer et al. | |
| 7,738,944 B2 | 6/2010 | Ho et al. | |
| 2009/0177076 A1* | 7/2009 | Aldefeld | G01R 33/5676 600/410 |
| 2016/0338614 A1* | 11/2016 | Gall | A61B 5/0555 |
| 2017/0059678 A1* | 3/2017 | Kannengiesser | G01R 33/543 |

* cited by examiner

*Primary Examiner* — Gregory H Curran
(74) *Attorney, Agent, or Firm* — The Small Patent Law Group LLC; Dean D. Small

(57) ABSTRACT

A magnetic resonance imaging (MRI) system includes a table and at least one processor. The table is configured to support a patient, and to travel along a length in a direction of movement through an imaging zone to at least one imaging position. A spatial gradient field varies for at least a portion of the imaging zone. The at least one processor is operably coupled to the table, and configured to obtain a spatial gradient field curve representing magnitude of the spatial gradient field as a function of position along the direction of movement; determine a table speed curve using the spatial gradient field curve, wherein the table speed varies along the direction of movement; and control movement of the table using the table speed curve.

20 Claims, 5 Drawing Sheets

SYSTEMS AND METHODS FOR TABLE MOVEMENT CONTROL

BACKGROUND OF THE INVENTION

The subject matter disclosed herein relates generally to apparatus and methods for providing table movement control, for example controlling movement of a patient table in a medical imaging system, such as a magnetic resonance imaging (MRI) system.

Table motion speed for MRI procedures is limited to avoid exposing patients to an overly large change in rate of magnetic field strength. However, certain conventional approaches for controlling table speed result in unduly slow table speed, lengthening the amount of time spent transporting a patient and lengthening the time of imaging procedures.

BRIEF DESCRIPTION OF THE INVENTION

In one example embodiment, a magnetic resonance imaging (MRI) system is provided that includes a table and at least one processor. The table is configured to support a patient, and to travel along a length in a direction of movement through an imaging zone to at least one imaging position. A spatial gradient field varies for at least a portion of the imaging zone. The at least one processor is operably coupled to the table, and configured to obtain a spatial gradient field curve representing magnitude of the spatial gradient field as a function of position along the direction of movement; determine a table speed curve using the spatial gradient field curve, wherein the table speed varies along the direction of movement; and control movement of the table using the table speed curve.

In another example embodiment, a method is provided that includes obtaining a spatial gradient field curve representing a magnitude of a spatial gradient field as a function of position along a length in a direction of movement through an imaging zone to at least one imaging position for a table of a magnetic resonance imaging (MRI) system. The spatial gradient field varies for at least a portion of the imaging zone. The method also includes determining a table speed curve using the spatial gradient field curve, wherein the table speed varies along the direction of movement. Further, the method includes controlling movement of the table using the table speed curve.

In another example embodiment, a tangible and non-transitory computer readable medium is provided that includes one or more software modules. The one or more software modules are configured to direct one or more processors to obtain a spatial gradient field curve representing a magnitude of a spatial gradient field as a function of position along a length in a direction of movement through an imaging zone to at least one imaging position for a table of a magnetic resonance imaging (MRI) system, wherein the spatial gradient field varies for at least a portion of the imaging zone; determine a table speed curve using the spatial gradient field curve, wherein the table speed varies along the direction of movement; and control movement of the table using the table speed curve.

DETAILED DESCRIPTION OF THE INVENTION

Figure 1:
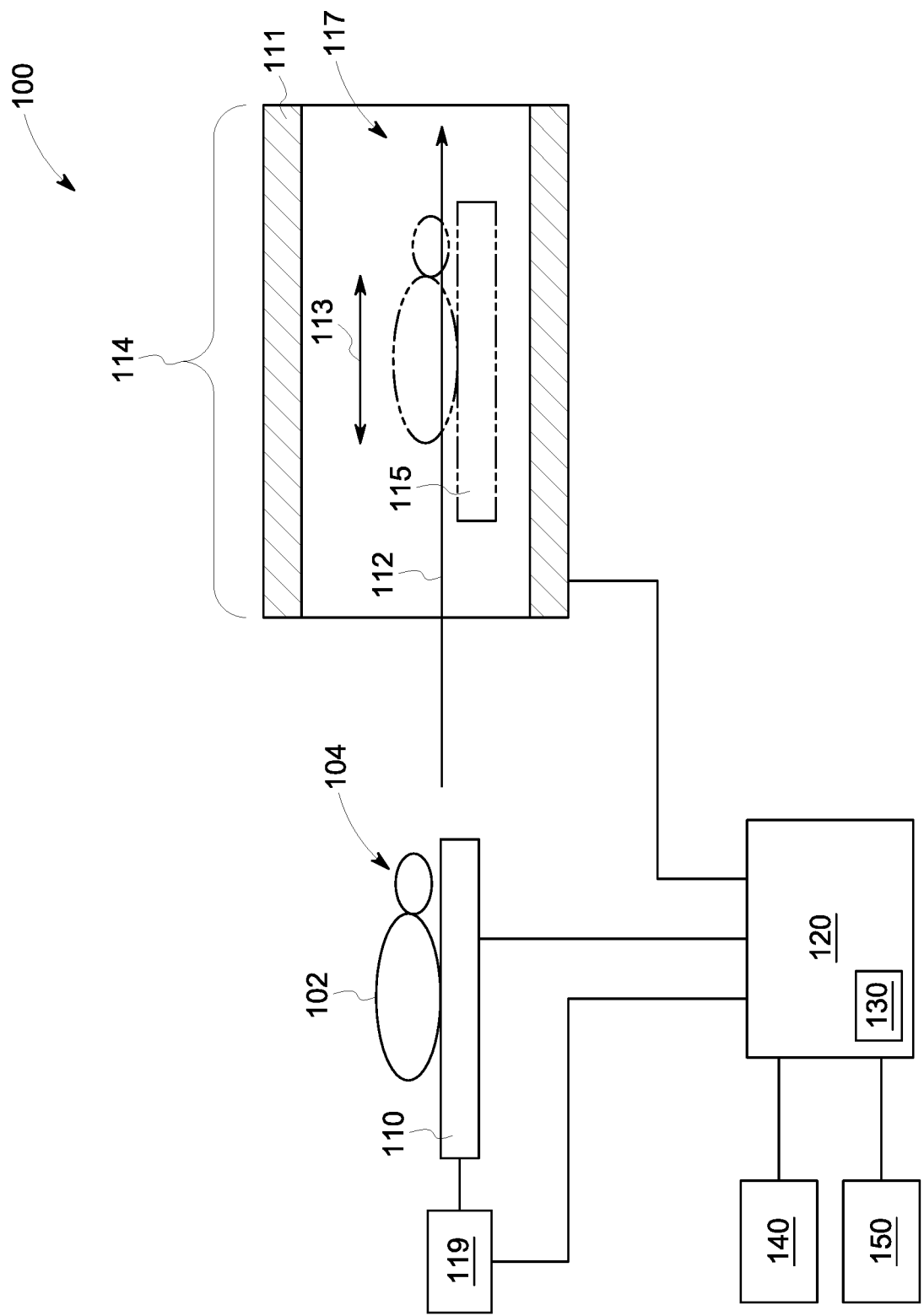
FIG. 1 provides a schematic block view of a magnetic resonance imaging (MRI) system in accordance with various embodiments.

The following detailed description of certain embodiments will be better understood when read in conjunction with the appended drawings. To the extent that the figures illustrate diagrams of the functional blocks of various embodiments, the functional blocks are not necessarily indicative of the division between hardware. It should be understood that the various embodiments are not limited to the arrangements and instrumentality shown in the drawings.

As used herein, an element or step recited in the singular and preceded with the word "a" or "an" should be understood as not excluding plural of said elements or steps, unless such exclusion is explicitly stated. Furthermore, references to "one embodiment" of are not intended to be interpreted as excluding the existence of additional embodiments that also incorporate the recited features. Moreover, unless explicitly stated to the contrary, embodiments "comprising" or "having" an element or a plurality of elements having a particular property may include additional elements not having that property.

Various embodiments provide improved control of table movement for imaging systems, such as magnetic resonance imaging (MRI) systems. Various embodiments provide for reduced travel times of patient tables by varying the speed along a course of travel based on the varying magnitude of the spatial gradient field along the course of travel.

Various embodiments provide for determination of a table speed curve based on a spatial gradient field curve, and control of table speed based on the table speed curve. By using the spatial gradient field at different locations along a course of travel, the speed in various embodiments is varied along the course of travel to provide reduced travel time while still addressing patient comfort.

A technical advantage of various embodiments includes improved performance of imaging systems. A technical advantage of various embodiments includes maintenance of patient comfort while providing reduced transportation times. A technical advantage of various embodiments includes providing flexibility for manual table speed control in addition to automatic table speed control.

FIG. 1 provides a schematic block view of a magnetic resonance imaging (MRI) system 100 in accordance with various embodiments. The depicted MRI system 100 includes a table 110 and a processing unit 120. The table 110 is configured to support a patient 102, and is configured to travel along a length 112 in a direction of movement 113 through an imaging zone 114 to at least one imaging position 115 (the imaging position 115 is shown in phantom lines in FIG. 1). Generally, the imaging zone 114 defined by the presence of magnets 111 for providing a field to be used for MR imaging. For example, the imaging zone 114 may be defined within the bore 117 of one or more magnets 111. It may be noted that different movements of the table 110 in and out of the imaging zone 114, or between positions in the imaging zone 114, may be utilized. For example, the movement of table 110 may be continuous from a starting position outside of the imaging zone 114 to a single discrete position (e.g., a single imaging position 115) in imaging zone 114. As another example, movement of the table 110 in various embodiments may be in a series of movements, such as a step and shoot movement between plural imaging positions 115 within the imaging zone 114 (e.g., for whole body imaging).

It may be noted that, as a practical matter, the magnetic field provided within the imaging zone 114 is not uniform, but instead varies through the imaging zone 114. Accordingly, the imaging zone 114 may be understood as having a spatial gradient field (e.g., variance of strength of field along the length 112 in the direction of movement 113). The spatial gradient field varies for at least a portion of the imaging zone 114.

Figure 2:
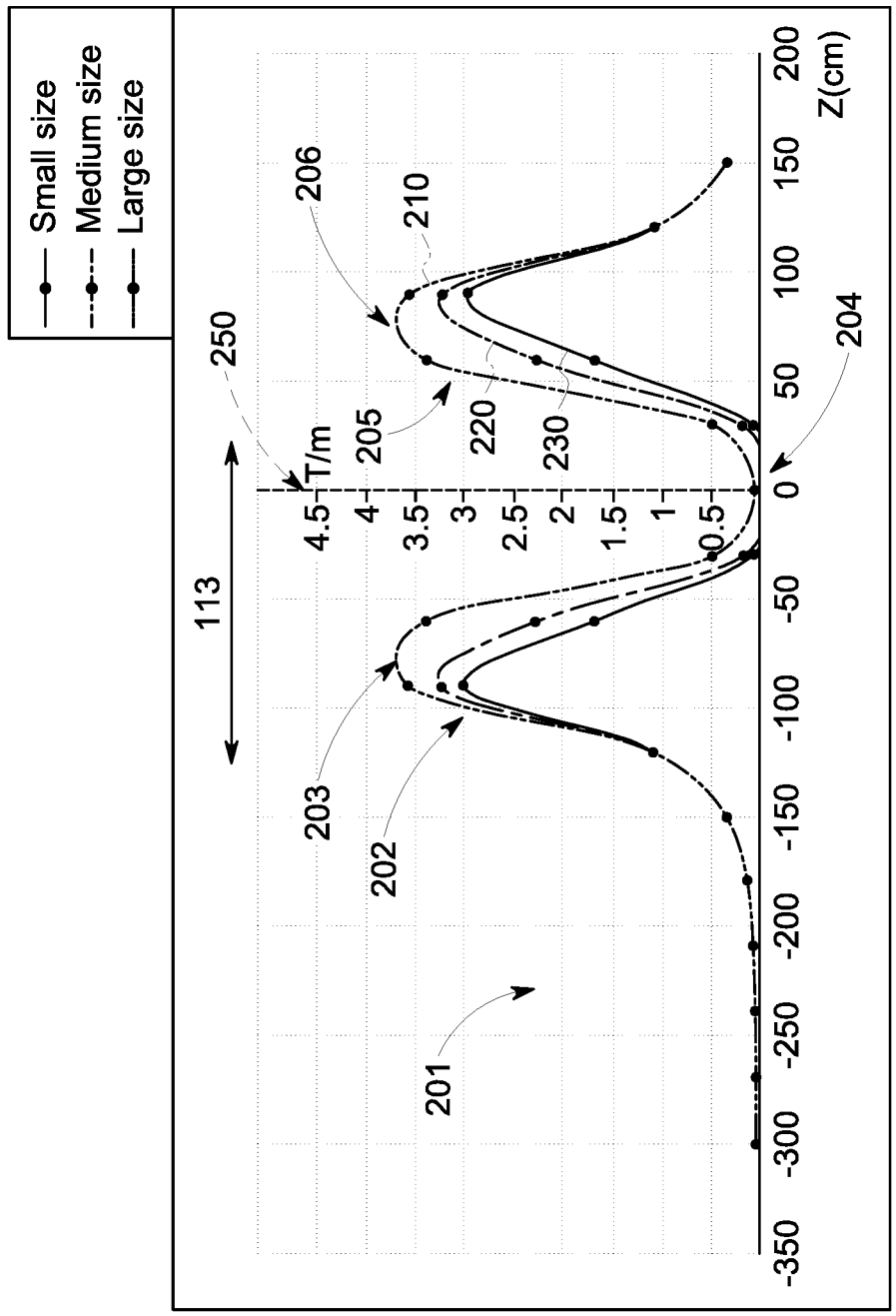
FIG. 2 provides a view of spatial gradient field curves in accordance with various embodiments.

FIG. 2 provides an example graph of spatial gradient fields that vary with linear position along a direction of movement 113. The horizontal axis in FIG. 2 is linear position (e.g., position along a z-axis along which the table 110 moves), and the vertical axis is spatial gradient field (in Tesla/meter (T/m) in the illustrated embodiment). It may be noted that the field experienced by the patient 102 may vary at different lengths along the patient. Generally, the effect of the field on the brain 104 of the patient 102 is of interest in determining tolerability to change in field. Accordingly, the positions shown for FIG. 2 may be understood as corresponding to the position of the brain 104 of the patient 102 along the z-axis or length 114 along the direction of movement 113. Further, the horizontal axis is labelled using an isocenter 250 of the field as 0, and negative and positive displacement values on either side of the isocenter.

It may further be noted that the magnitude of the gradient varies with patient size, with the gradient being larger for larger patients. Accordingly, three gradient curves are shown in FIG. 2, namely a first curve 210 for a larger patient, a second curve 220 for a medium sized patient, and a third curve 230 for a small patient. As seen in FIG. 2, for the illustrated example, each of the curves 210, 220, and 230 have a generally similar shape. For example, at an entry portion 201 from −300 centimeters to −200 centimeters, the gradient is zero or close to zero. It may be noted that the particular values for position and/or gradient strength provided in connection with FIG. 2 are by way of example for illustrative purposes, and that other embodiments may utilize other values and/or curve shapes. For example, the curves of FIG. 2 correspond to gradients for an example 1.5T system. The entry portion 201 corresponds to a range of positions at which the brain 104 of the patient 102 is entirely or nearly entirely out of the magnetic field of the imaging zone 114.

Next, a first portion 202 of each gradient curve starting at about −200 centimeters corresponds to a portion where the brain 104 enters the imaging zone and approaches the isocenter 250. At about −80 centimeters of the illustrated example, the gradient reaches a peak 203 and then decreases as the curve more closely approaches the isocenter 250.

A second portion 204 of each gradient curve is located within about 20 centimeters of the isocenter 250 on either side of the isocenter 250 and corresponds to a position at which the brain 104 of the patient 102 is at or near the isocenter 250. For the second portion 204, the gradient is at zero or a relatively low value.

If the brain 104 of the patient 102 is advanced further past the isocenter 250, a third portion 205 of each curve is encountered. At about 80 centimeters of the illustrated example, the gradient reaches a peak 206 and then decreases as the brain 104 approaches a far edge of the field within the imaging zone 114 past the isocenter 250.

As seen in the example of FIG. 2, the gradient varies along the length 112 in the direction of movement 113. It may be noted that patient comfort is generally correlated with change in field over time instead of distance, however. Accordingly, the processing unit 120 in the illustrated embodiments is configured (e.g., programmed) to control the table at a varying speed. For example, the patient 102 may be moved more quickly through portions at which the spatial gradient field is relatively low (e.g., the entry portion 201 and the second portion 204) and more slowly through portions at which the spatial gradient field is relatively high (e.g., the first portion 202 and the third portion 205).

More specifically, in the illustrated example, the processing unit 120 is operably coupled to the table 110 (e.g., is communicably coupled with an actuation portion 119 of the table 110 and configured to provide control signals to the actuation portion 119 to move the table 110, and/or configured to receive information from the table 110 regarding movement of the table 110). The depicted processing unit 120 is also configured to obtain a spatial gradient field curve representing magnitude of the spatial gradient field as a function of position along the direction of movement 113, to determine a table speed curve using the spatial gradient field curve (with the table speed varying along the direction of movement 113 for the table speed curve), and to control movement of the table 110 using the table speed curve.

In various embodiments the processing unit 120 includes processing circuitry configured to perform one or more tasks, functions, or steps discussed herein. In various embodiments, the processing unit 120 may additionally control one or more aspects of the MRI system 100 to acquire imaging information and/or to reconstruct an image using imaging information acquired by the MRI system 100. It may be noted that "processing unit" as used herein is not intended to necessarily be limited to a single processor or computer. For example, the processing unit 120 may include multiple processors, ASIC's, FPGA's, and/or computers, which may be integrated in a common housing or unit, or which may distributed among various units or housings. It may be noted that operations performed by the processing unit 120 (e.g., operations corresponding to process flows or methods discussed herein, or aspects thereof) may be sufficiently complex that the operations may not be performed by a human being within a reasonable time period. For example, the determination of a table speed curve and generation of corresponding control signals may rely on or utilize computations that may not be completed by a person within a reasonable time period.

The depicted processing unit 120 includes a memory 130. The memory 130 may include one or more computer readable storage media. The memory 130, for example, may store information regarding system properties (e.g., information regarding the spatial gradient), precalculated curves (e.g., predetermined spatial gradient field curves and/or table speed curves based on patient size), algorithms or processes for determining spatial gradient field curves and/or table speed curves, or the like. Further, the process flows and/or flowcharts discussed herein (or aspects thereof) may represent one or more sets of instructions that are stored in the memory 130 for direction of operations of the MRI system 100.

Figure 3:
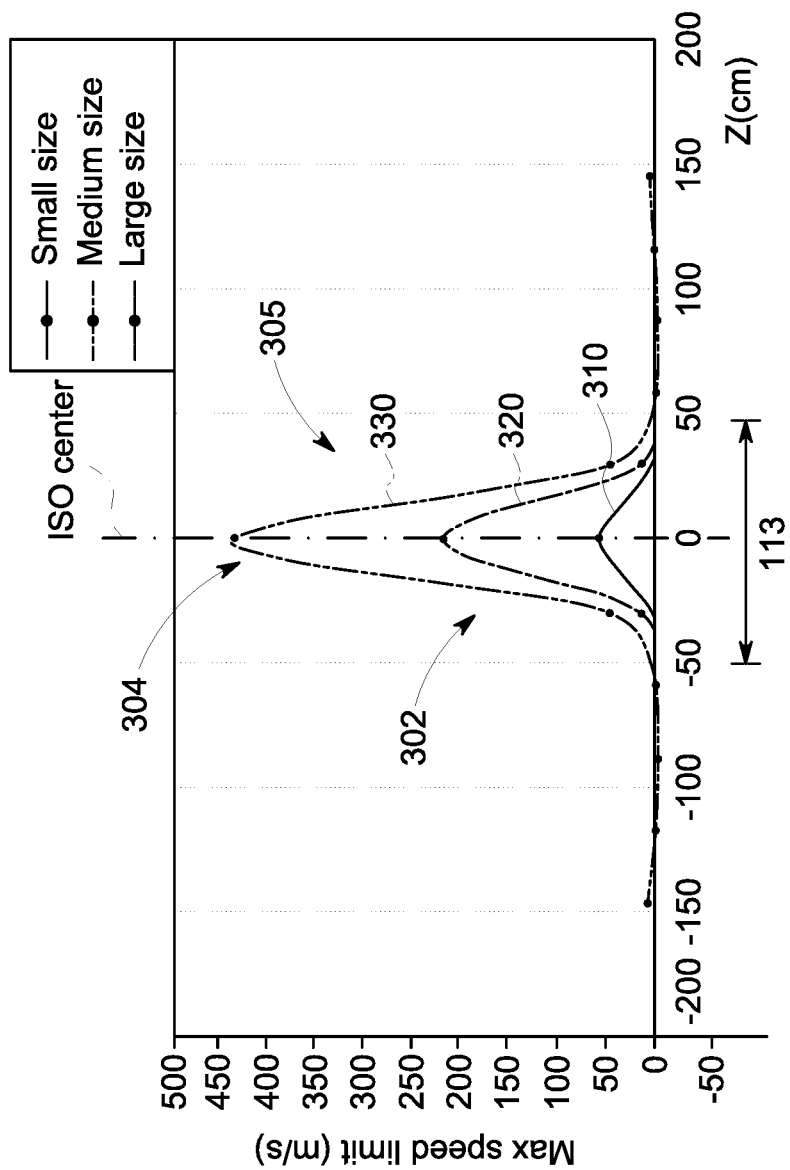
FIG. 3 provides a view of table speed curves in accordance with various embodiments.

FIG. 2 (discussed above) provides example spatial gradient field curves, and FIG. 3 provides example table speed curves. Generally, the table speed curve in various embodiments may be determined using a corresponding spatial gradient field curve and a target temporal rate of field change, or desired (or tolerated) maximum field strength temporal rate change value. The field strength temporal rate change may be understood as the change over time of the field experienced by the brain 104 of the patient 102 as the patient 102 moves through the imaging zone 114. The maximum field strength temporal rate change value in various embodiments is a predetermined value based on an established standard (e.g., set at the standard or at a percentage of the standard). For example, a standard of 3T/s may be used as the maximum field strength temporal rate change value.

With the spatial gradient field curve obtained by the processing unit 120 (e.g., from a previously performed or otherwise known calibration or test of the MRI system 100), the processing unit 120 may then determine the table speed curve. For example, the table speed curve may be determined by dividing the maximum field strength temporal rate change by the spatial gradient field field. Because the spatial gradient field field varies with position (e.g., linear position along a z-axis) while the maximum field strength temporal rate change is constant, the resulting table speed curve also varies with position, varying inversely with the spatial gradient field.

Three table speed curves are shown in FIG. 3—a first table speed curve 310 corresponding to or determined using the first curve 210 (and accordingly for a large patient), a second table speed curve 320 corresponding to or determined using the second curve 220 (and accordingly for a medium sized patient), and a third table speed curve 330 corresponding to or determined using the third curve 230 (and accordingly for a small patient). As seen in FIG. 3, because the spatial gradient field is higher for the larger patient, the first table speed curve 310 includes lower speeds than the other curves. Generally, the speed set forth by each curve is lower where the gradient is high, and higher where the gradient is low. The curves of FIG. 3 are shown from a range of about −150 centimeters to about 150 centimeters, and, accordingly, each curve 310, 320, 330 includes a first portion 302 corresponding to the first portion 202 of the curve of FIG. 2, a second portion 304 corresponding to the second portion 204, and a third portion 305 corresponding to the third portion 205. (It may be noted that a portion corresponding to the entry portion 201 is omitted from FIG. 3, and that the speed may be relatively high during the entry portion 201 as there is little or no field there.) As seen in FIGS. 2 and 3, the shape of the table speed curves varies inversely with the shape of the spatial gradient field curves, with the table speed relatively high when the spatial gradient field is relatively low, and the table speed relatively low when the spatial gradient field is relatively high. It may be noted that a maximum speed may also be limited by an absolute ceiling or upper limit independent of spatial gradient field. For example where the spatial gradient field is zero or low (such as the entry portion 201), a table speed limit may be selected based on patient comfort resulting from speed alone. It may further be noted that the example of FIG. 3 is discussed in connection with a 1.5T MRI system. However, the same principles may be applied, for example, to systems with stronger fields, such as 3T or 7T systems.

It may be noted that the speed of the table 110 throughout its range of motion may in some examples be the speed specified by the table speed curve for particular locations along its range of motion, or may be one or more speeds derived from the table speed curve. It may further be noted that, in various embodiments, the spatial gradient field curve and/or table speed curve may be obtained or determined using predetermined curves, for example based on patient properties (e.g., size of patient) and/or system properties (e.g., as determined by a previously performed calibration or measurement). In some embodiments, a group of predetermined curves are stored in memory 130 or otherwise accessible to the processing unit 120, and one or more appropriate curves may be selected based on conditions for a particular imaging process. In some embodiments, the processing unit 120 may use patient size to obtain the spatial gradient field curve, for example, by selecting a spatial gradient field curve to be used from an available group of curves (e.g., curves 210, 220, 230) based on patient size.

With the table speed curve determined, the processing unit 120 controls movement of the table 110 using the table speed curve. For example, the processing unit 120 may send control signals to the table 110 (e.g., actuation portion 119 of the table 110) to move the table 110 into or out of the imaging zone 114. For example, to improve or optimize movement time, the table 110 may be controlled to move more quickly where the spatial gradient field is low, and more slowly where the spatial gradient field is high, to keep the time rate of change of field experienced by the patient 102 at or near a predetermined maximum.

In various embodiments, the processing unit 120 is configured to obtain a user input, and to control movement of the table 110 using the user input. For example, the MIl system 100 may include an input unit 110 (e.g., keyboard, mouse, touchscreen, or the like) configured to allow a user to provide the user input to the processing unit 120. The user input may be used to specify or alter a table speed. In various embodiments, the MRI system 100 includes a display unit 150 that provides guidance to a user providing input specifying or adjusting a table speed, which the user provides via the input unit 140. The display unit 150, for example may be a screen. (It may be noted that the display unit 150 and input unit 140 may be integrated into a single device, such as a touchscreen.) The display unit 150 in various embodiments is used to show a user one or more curves indicating maximum speed and/or gradient, and/or one or more displays comparing current speed and/or current spatial gradient field to the maximum allowable, allowing a user to see how close current conditions are to the maximum allowable. The display in various embodiments may be color-coded (e.g., displaying a green light or image for a relatively large difference between current speed and maximum allowable, a yellow light or image for smaller difference between current speed and maximum allowable, or a red light or image for little or no difference between current speed and maximum allowable). Accordingly, the display unit 150 may be utilized to provide information or updates regarding an automatically controlled table movement, and/or guidance (including warnings) regarding manual control of the table 110.

In some embodiments, a maximum allowable speed from the table speed curve for each location along the movement of the table 110 may be used as a limit which a user input is not allowed to override. As another example, a user input may be used to modify a predetermined control scheme. In some embodiments, an automatically generated control scheme may be used to provide a default speed, with a user input used to override the default speed.

It may be noted that various embodiments use one or more control modes or modes of operation for controlling the table speed based on the table speed curve as discussed herein. The modes of operation may include modes that use automatic or autonomous control of table speed, modes that utilize user input, and/or modes that utilize a combination of autonomous and manual control. For example, in various embodiments, the processing unit 120 is configured to select a mode of operation to control movement of the table from a plurality of modes of operation. The particular mode of operation may be selected based on procedure, patient characteristics, and/or user preferences, for example. Each mode of operation may utilize the speed curve differently to determine a control scheme for moving the table.

In one example mode of operation, the processing unit 120 is configured to control movement of the table 110 at speed specified by the table speed curve, with the speed at a given position (e.g., defined by the location of the brain of the patient) being the speed specified at the corresponding location on the table speed curve. Accordingly, the speed of the table 110 may vary the same as the table speed curve varies. With the table 110 automatically or autonomously following a table speed curve that specifies the maximum speed at each location along the movement, the overall movement time will be minimized. Alternatively, the speed of the table 110 may be modified from the values specified by the table speed curve (e.g., the table speed may be 90%, or another predetermined percentage, of the corresponding table speed curve value for the corresponding location).

In another example mode of operation, the processing unit 120 is configured to control movement of the table 110 at a constant speed based on a minimum speed from the table speed curve. The minimum speed may be defined as the maximum allowable speed for the location of the highest spatial gradient field, which will be the minimum speed on a table speed curve defined by the maximum temporal rate change permissible divided by the spatial gradient field curve. Accordingly, an automatic or autonomous control scheme may be provided that sets a constant speed during patient transportation, providing an economic control method.

In a third example mode of operation, the processing unit is configured to control movement of the table 110 using a default speed specified by the table speed curve, and to control movement of the table 110 at a reduced speed responsive to a user input. This mode may be referred to as a mild table movement mode. This mode provides manual adjustment, for example by pressing a deceleration button. This mode may be particularly useful, for example, for sensitive patients experiencing feelings of vertigo and/or nausea at speeds approaching the permissible standard.

Figure 4:
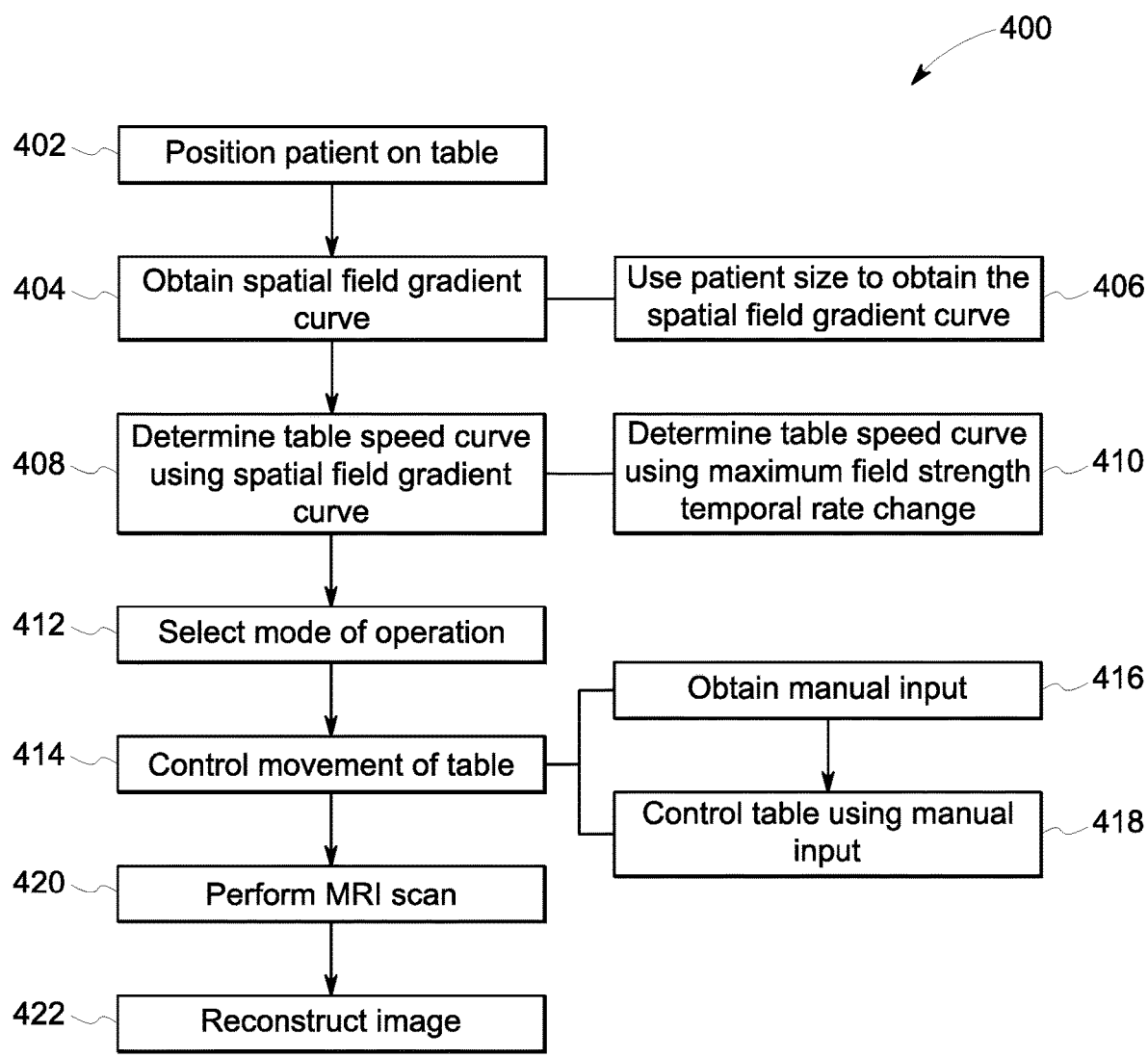
FIG. 4 provides a flowchart of a method in accordance with various embodiments.

FIG. 4 provides a flowchart of a method 400 (e.g., for moving a patient table in an MRI system), in accordance with various embodiments. The method 400, for example, may employ or be performed by structures or aspects of various embodiments (e.g., systems and/or methods and/or process flows) discussed herein. In various embodiments, certain steps may be omitted or added, certain steps may be combined, certain steps may be performed concurrently, certain steps may be split into multiple steps, certain steps may be performed in a different order, or certain steps or series of steps may be re-performed in an iterative fashion. In various embodiments, portions, aspects, and/or variations of the method 400 may be able to be used as one or more algorithms to direct hardware (e.g., one or more aspects of the processing unit 120) to perform one or more operations described herein.

At 402, a patient is positioned on a table (e.g., table 110). The position of the brain of the patient in various embodiments may be placed at a predetermined portion of table, or the position of the brain with respect to a landmark on the table may be noted, so that the position of the brain with respect to a field within an imaging zone is known as the table moves through the imaging zone. Accordingly, the effect of the spatial gradient field on the brain of the patient may be determined as the patient travels through the imaging zone and may be utilized to determine table speed as discussed herein. In the illustrated embodiment, the table is configured to move along a length in a direction of movement through an imaging zone to at least one imaging position.

It may be noted that the spatial gradient field varies along the length in the direction of movement for at least a portion of the imaging zone (see, e.g., FIG. 2 and related discussion). At 404, a spatial gradient field curve is obtained. The spatial gradient field curve represents the magnitude of the spatial gradient field as a function of position along the length in the direction of movement. The spatial gradient field curve may be obtained through a calculation based on system properties and/or configuration for a given procedure, and/or may be obtained from an archive containing one or more stored curves based on previous calibrations and/or measurements. In the illustrated embodiment, at 406, patient size is used to obtain the spatial gradient field curve. For example, a group of spatial gradient field curves for differently sized patients may be stored (e.g., in memory 130), and the patient size may be entered (e.g., via input unit 140) before an imaging process. The spatial gradient curve for the archived size most similar to the patient size may then be selected from among the curves and used.

At 408, a table speed curve (see, e.g., FIG. 3) is determined using the spatial gradient field curve. The table speed specified by the table speed curve varies along the direction of movement, for example to account for changes in the spatial gradient field. In various embodiments, the table speed curve specifies maximum table speeds along the length in the direction of movement such that the specified speed and the corresponding magnitude of the spatial gradient field at each location along the length satisfies a predetermined maximum value (e.g., as set forth by a standard), for example to help ensure patient comfort. For example, in some embodiments, a predetermined maximum field strength temporal rate change value may be used to determine the table speed curve. In the illustrated embodiment, at 410, the table speed curve is determined by using the spatial gradient field curve and a predetermined maximum field strength temporal rate change value (e.g., by dividing the predetermined maximum field strength temporal rate change value by the spatial gradient field curve).

At 412 of the illustrated embodiment, a mode of operation to control movement of the table is selected from a plurality of modes of operation. The particular mode of operation may be selected based on an imaging procedure to be performed, patient characteristics, and/or operator preference. For example, where reduced time of procedure is prioritized, a mode of operation that controls the table automatically or autonomously at a maximum speed for each location along the length of the movement as specified by the table speed curve may be selected. As another example, where a patient is known to be sensitive to movement in the field, a mode of operation may be selected that sets forth a default speed but allows for manual input to slow the table down.

At 414, the movement of the table is controlled using the table speed curve. The movement may be performed as a single movement from outside of the imaging zone to a single imaging position within the imaging zone, or may be performed in a series of steps between plural imaging positions. The table speed may be controlled to be at the table speed value specified by the table speed curve. Alternatively, one or more of the speeds specified by the table speed curve may be modified, either as part of an automatic control scheme (e.g., by controlling the table to move at a predetermined percentage of speed specified by the table speed control curve, or modifying the speeds automatically, for example to conform to a maximum speed limit based on individual patient comfort or practitioner preference), or as part of a control scheme also using manual inputs (e.g., by allowing a manual input to override or modify a predetermined control scheme, for example to allow deceleration if a patient exhibits discomfort during the movement of the table). At 416 of the illustrated embodiment, a manual input is obtained, and at 418 the movement of the table is controlled using the manual input.

At 420, with the patient positioned as desired, an MRI scan is performed, and at 422 an image is reconstructed using data acquired during the MRI scan performed at 420.

Figure 5:
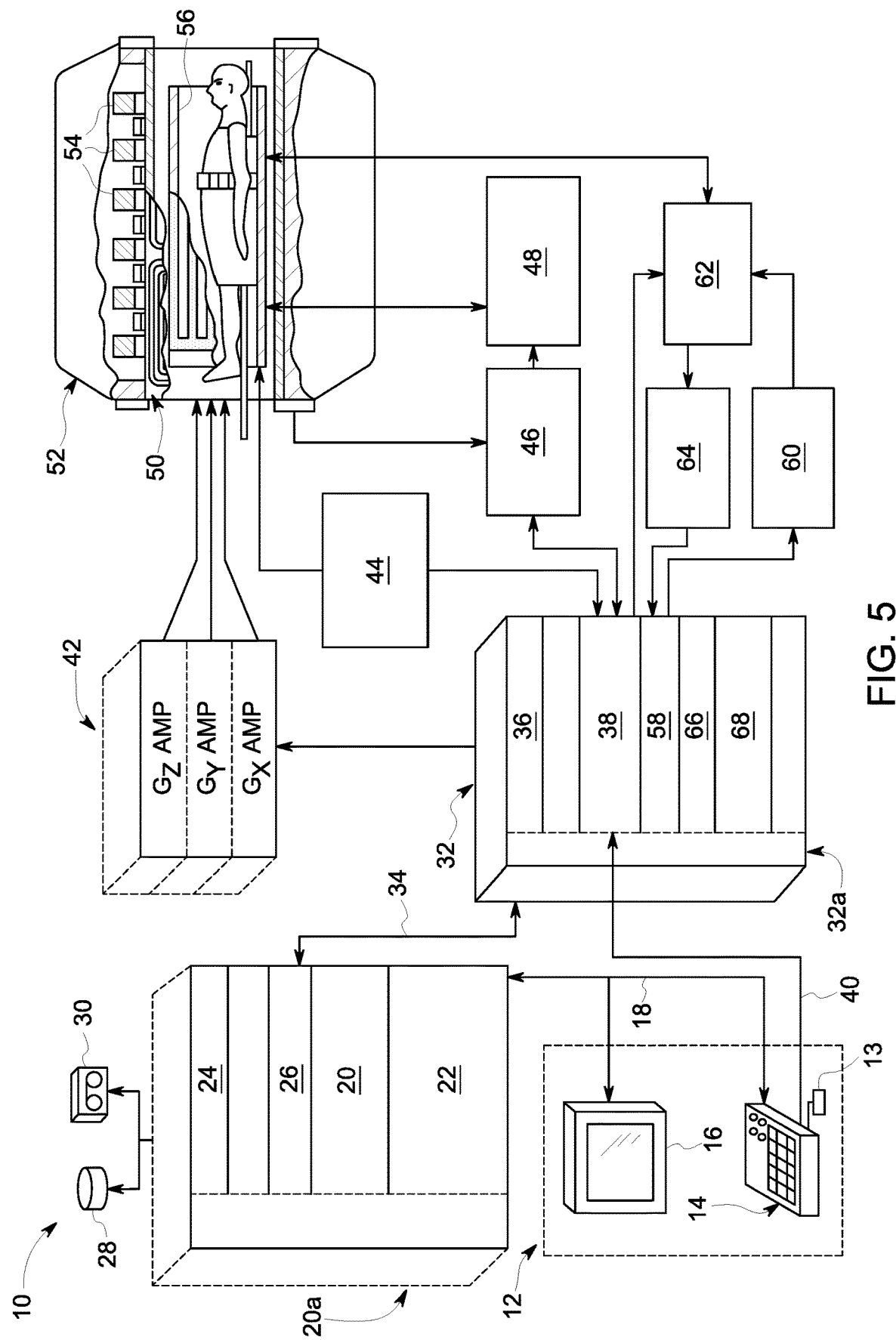
FIG. 5 provides a schematic view of a magnetic resonance imaging (MRI) system in accordance with various embodiments.

As discussed herein various methods and/or systems (and/or aspects thereof) described herein may be implemented in connection with an MRI system. For example, FIG. 5 depicts various major components of an MRI system 10 formed in accordance with various embodiments. The operation of the system is controlled from an operator console 12 which includes a keyboard or other input device 13, a control panel 14, and a display 16. The console 12 communicates through a link 18 with a separate computer system 20 that enables an operator to control the production and display of images on the screen 16. The computer system 20 includes a number of modules which communicate with each other through a backplane 20a. These include an image processor module 22, a CPU module 24 and a memory module 26, known in the art as a frame buffer for storing image data arrays. The computer system 20 is linked to disk storage 28 and recordable media 30 for storage of image data and programs, and communicates with a separate system control 32 through a high speed serial link 34. The input device 13 can include a mouse, joystick, keyboard, track ball, touch activated screen, light want, voice control, or any similar or equivalent input device, and may be used for interactive geometry prescription.

The system control 32 includes a set of modules connected together by a backplane 32a. These include a CPU module 36 and a pulse generator module 38 which connects to the operator console 12 through a serial link 40. It is through link 40 that the system control 32 receives commands from the operator to indicate the san sequence that is to be performed. The pulse generator module 38 operates the system components to carry out the desired scan sequence and produce data which indicates the timing, strength and shape of the RF pulses produced, and the timing and length of the data acquisition window. The pulse generator module 38 connects to a set of gradient amplifiers 42, to indicate the timing and shape of the gradient pulses that are produced during the scan. The pulse generator module 38 can also receive patient data from a physiological acquisition controller 44 that receives signals from a number of different sensor connected to the patient or subject, such as ECG signals from electrodes attached to the patient. And finally, the pulse generator module 38 connects to a scan room interface circuit 46 which receives signals from various sensors associated with the condition of the patient and the magnet system. It is also through the scan room interface circuit 46 that a patient positioning system 48 receives commands to move the patient to the desired position for the scan.

The gradient waveforms produced by the pulse generator module 38 are applied to the gradient amplifier system 42 having $G_x$, $G_y$, and $G_z$ amplifiers. Each gradient amplifier excites a corresponding physical gradient coil in a gradient coil assembly 50 generally designated to produce the magnetic field gradients used for spatially encoding acquired signals. The gradient coil assembly 50 and RF shield (not shown) form a part of a magnet assembly 52 which includes a polarizing magnet 54 and a RF coil assembly 56. A transceiver module 58 in the system control 32 produces pulses which are amplified by an RF amplifier 60 and coupled to the RF coil assembly 56 by a transmit/receive switch 62. The resulting signals emitted by the excited nuclei in the patient may be sensed by the same RF coil assembly 56 or apportion thereof and coupled through transmit/receive switch 62 to a preamplifier 64. The amplified MR signals are demodulated, filtered, and digitized in the receive section of the transceiver 58. The transmit/receive switch 62 is controlled by a signal from the pulse generator module 38 to electrically connect the RF amplifier 60 to the coil assembly 56 during the transmit mode and to connect the preamplifier 64 to the coil assembly 56 during the receive mode. The transmit/receive switch 62 can also enable a separate RF coil (for example, a surface coil) to be used in either the transmit or receive mode. The magnet assembly 52 may be cooled cryogenically.

The MR signals picked up by the selected RF coil are digitized by the transceiver module 58 and transferred to a memory module 66 in the system control 32. A scan is complete when an array of raw k-space data has been acquired in the memory module 66. This raw k-space data is rearranged into separate k-space data arrays for each image to be reconstructed, and each of these is input to an array processor 68 which operates to Fourier transform the data into an array of image data. This image data is conveyed through the serial link 34 to the computer system 20 where it is stored in memory, such as disk storage 28. In response to commands received from the operator console 12, this image data may be archived in long term storage, such as on the tape drive 30, or it may be further processed by the image processor 22 and conveyed to the operator console 12 and presented on the display 16.

It should be noted that the various embodiments may be implemented in hardware, software or a combination thereof. The various embodiments and/or components, for example, the modules, or components and controllers therein, also may be implemented as part of one or more computers or processors. The computer or processor may include a computing device, an input device, a display unit and an interface, for example, for accessing the Internet. The computer or processor may include a microprocessor. The microprocessor may be connected to a communication bus. The computer or processor may also include a memory. The memory may include Random Access Memory (RAM) and Read Only Memory (ROM). The computer or processor further may include a storage device, which may be a hard disk drive or a removable storage drive such as a solid-state drive, optical disk drive, and the like. The storage device may also be other similar means for loading computer programs or other instructions into the computer or processor.

As used herein, the term "computer" or "module" may include any processor-based or microprocessor-based system including systems using microcontrollers, reduced instruction set computers (RISC), ASICs, logic circuits, and any other circuit or processor capable of executing the functions described herein. The above examples are exemplary only, and are thus not intended to limit in any way the definition and/or meaning of the term "computer".

The computer or processor executes a set of instructions that are stored in one or more storage elements, in order to process input data. The storage elements may also store data or other information as desired or needed. The storage element may be in the form of an information source or a physical memory element within a processing machine.

The set of instructions may include various commands that instruct the computer or processor as a processing machine to perform specific operations such as the methods and processes of the various embodiments. The set of instructions may be in the form of a software program. The software may be in various forms such as system software or application software and which may be embodied as a tangible and non-transitory computer readable medium. Further, the software may be in the form of a collection of separate programs or modules, a program module within a larger program or a portion of a program module. The software also may include modular programming in the form of object-oriented programming. The processing of input data by the processing machine may be in response to operator commands, or in response to results of previous processing, or in response to a request made by another processing machine.

As used herein, a structure, limitation, or element that is "configured to" perform a task or operation is particularly structurally formed, constructed, or adapted in a manner corresponding to the task or operation. For purposes of clarity and the avoidance of doubt, an object that is merely capable of being modified to perform the task or operation is not "configured to" perform the task or operation as used herein. Instead, the use of "configured to" as used herein denotes structural adaptations or characteristics, and denotes structural requirements of any structure, limitation, or element that is described as being "configured to" perform the task or operation. For example, a processing unit, processor, or computer that is "configured to" perform a task or operation may be understood as being particularly structured to perform the task or operation (e.g., having one or more programs or instructions stored thereon or used in conjunction therewith tailored or intended to perform the task or operation, and/or having an arrangement of processing circuitry tailored or intended to perform the task or operation). For the purposes of clarity and the avoidance of doubt, a general purpose computer (which may become "configured to" perform the task or operation if appropriately programmed) is not "configured to" perform a task or operation unless or until specifically programmed or structurally modified to perform the task or operation.

As used herein, the terms "software" and "firmware" are interchangeable, and include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the various embodiments without departing from their scope. While the dimensions and types of materials described herein are intended to define the parameters of the various embodiments, they are by no means limiting and are merely exemplary. Many other embodiments will be apparent to those of skill in the art upon reviewing the above description. The scope of the various embodiments should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. § 112(f) unless and until such claim limitations expressly use the phrase "means for" followed by a statement of function void of further structure.

This written description uses examples to disclose the various embodiments, including the best mode, and also to enable any person skilled in the art to practice the various embodiments, including making and using any devices or systems and performing any incorporated methods. The patentable scope of the various embodiments is defined by the claims, and may include other examples that occur to those skilled in the art. Such other examples are intended to be within the scope of the claims if the examples have structural elements that do not differ from the literal language of the claims, or the examples include equivalent structural elements with insubstantial differences from the literal language of the claims.

What is claimed is:

1. A magnetic resonance imaging (MRI) system comprising:
    a table configured to support a patient, the table configured to travel along a length in a direction of movement through an imaging zone to at least one imaging position, wherein a spatial gradient field varies for at least a portion of the imaging zone; and
    at least one processor operably coupled to the table, the at least one processor configured to:
    obtain a spatial gradient field curve representing a magnitude of the spatial gradient field as a function of position along the direction of movement;
    determine a table speed curve using the spatial gradient field curve, wherein a table speed specified by the table speed curve varies along the direction of movement; and
    control movement of the table using the table speed curve.

2. The MRI system of claim 1, wherein the at least one processor is configured to determine the table speed curve using the spatial gradient field curve and a predetermined maximum field strength temporal rate change value.

3. The MRI system of claim 1, wherein the at least one processor is configured to use patient size to obtain the spatial gradient field curve.

4. The MRI system of claim 1, wherein the at least one processor is configured to obtain a user input, and to control movement of the table using the user input.

5. The MRI system of claim 1, wherein the at least one processor is configured to select a mode of operation to control movement of the table from a plurality of modes of operation.

6. The MRI system of claim 1, wherein the at least one processor is configured to control movement of the table at speeds specified by the table speed curve.

7. The MRI system of claim 1, wherein the at least one processor is configured to control movement of the table at a constant speed based on a minimum speed from the table speed curve.

8. The MRI system of claim 1, wherein the at least one processor is configured to control movement of the table using a default speed specified by the table speed curve, and to control movement of the table at a reduced speed responsive to a user input.

9. A method comprising:
   obtaining a spatial gradient field curve representing magnitude of a spatial gradient field as a function of position along a length in a direction of movement through an imaging zone to at least one imaging position for a table of a magnetic resonance imaging (MRI) system, wherein the spatial gradient field varies for at least a portion of the imaging zone;
   determining a table speed curve using the spatial gradient field curve, wherein a table speed specified by the table speed curve varies along the direction of movement; and
   controlling movement of the table using the table speed curve.

10. The method of claim 9, comprising determining the table speed curve using the spatial gradient field curve and a predetermined maximum field strength temporal rate change value.

11. The method of claim 9, comprising using patient size to obtain the spatial gradient field curve.

12. The method of claim 9, further comprising obtaining a user input, and controlling movement of the table using the user input.

13. The method of claim 9, comprising selecting a mode of operation to control movement of the table from a plurality of modes of operation.

14. The method of claim 9, comprising controlling movement of the table at speeds specified by the table speed curve.

15. The method of claim 9, comprising controlling movement of the table at a constant speed based on a minimum speed from the table speed curve.

16. The method of claim 9, comprising controlling movement of the table using a default speed specified by the table speed curve, and controlling movement of the table at a reduced speed responsive to a user input.

17. A tangible and non-transitory computer readable medium comprising one or more software modules configured to direct one or more processors to:
   obtain a spatial gradient field curve representing magnitude of a spatial gradient field as a function of position along a length in a direction of movement through an imaging zone to at least one imaging position for a table of a magnetic resonance imaging (MRI) system, wherein the spatial gradient field varies for at least a portion of the imaging zone;
   determine a table speed curve using the spatial gradient field curve, wherein a table speed specified by the table speed curve varies along the direction of movement; and
   control movement of the table using the table speed curve.

18. The tangible and non-transitory computer readable medium of claim 17, wherein the one or more software modules are configured to direct the one or more processors to determine the table speed curve using the spatial gradient field curve and a predetermined maximum field strength temporal rate change value.

19. The tangible and non-transitory computer readable medium of claim 17, wherein the one or more software modules are configured to direct the one or more processors to use patient size to obtain the spatial gradient field curve.

20. The tangible and non-transitory computer readable medium of claim 17, wherein the one or more software modules are configured to direct the one or more processors to obtain a user input, and control movement of the table using the user input.

\* \* \* \* \*